(12) United States Patent  (10) Patent No.: US 7,955,457 B2
Middlesworth et al.  (45) Date of Patent: Jun. 7, 2011

(54) ELASTIC LAMINATES AND METHODS OF MANUFACTURING SAME

(75) Inventors: Jeffrey Alan Middlesworth, Wauconda, IL (US); Bryan L. Matte, Kenosha, WI (US)

(73) Assignee: Tredegar Film Products Corp., Richmond, VA (US)

( * ) Notice: Subject to any disclaimer, the term of this patent is extended or adjusted under 35 U.S.C. 154(b) by 200 days.

(21) Appl. No.: 12/151,665

(22) Filed: May 8, 2008

(65) Prior Publication Data

US 2008/0216937 A1  Sep. 11, 2008

Related U.S. Application Data

(62) Division of application No. 11/563,953, filed on Nov. 28, 2006.

(60) Provisional application No. 60/740,036, filed on Nov. 28, 2005.

(51) Int. Cl.
*B32B 37/00* (2006.01)
(52) U.S. Cl. .................. 156/73.1; 156/229; 156/244.11
(58) Field of Classification Search .................. 156/73.1, 156/161, 163, 164, 229, 285, 286, 308.2, 156/308.4, 244.11; 264/442, 443, 444
See application file for complete search history.

(56) References Cited

U.S. PATENT DOCUMENTS

| 4,223,059 | A | * | 9/1980 | Schwarz ....................... 428/198 |
| 4,720,415 | A | * | 1/1988 | Vander Wielen et al. ..... 428/152 |
| 6,537,930 | B1 | * | 3/2003 | Middlesworth et al. ........ 442/39 |
| 6,720,279 | B2 | | 4/2004 | Cree et al. |
| 7,351,297 | B2 | * | 4/2008 | Middlesworth et al. ..... 156/73.1 |
| 7,674,733 | B2 | | 3/2010 | Wu |
| 2002/0192268 | A1 | | 12/2002 | Alwattari et al. |
| 2003/0105446 | A1 | | 6/2003 | Hutson et al. |
| 2004/0166756 | A1 | | 8/2004 | Kurihara et al. |
| 2005/0106980 | A1 | | 5/2005 | Abed et al. |

FOREIGN PATENT DOCUMENTS

| EP | 1304409 A1 | 4/2003 |
| JP | 2002013056 | 1/2002 |
| JP | 2003533374 A | 11/2003 |
| WO | 9512488 | 11/1993 |
| WO | WO 01/87592 A1 | 11/2001 |
| WO | WO 02/31245 A2 | 4/2002 |
| WO | 2005/019515 A1 | 3/2005 |

* cited by examiner

*Primary Examiner* — James Sells
(74) *Attorney, Agent, or Firm* — Tessari Patent Law Group, PLLC

(57) ABSTRACT

A method for forming an elastic laminate comprising: bonding a first nonwoven to an elastic film to form a laminate; activating the laminate to form an activated laminate; and bonding a consolidated nonwoven to the elastic film of the activated laminate to form the elastic laminate.

10 Claims, 2 Drawing Sheets

ELASTIC LAMINATES AND METHODS OF MANUFACTURING SAME

REFERENCE TO RELATED APPLICATION

This application claims priority to pending U.S. patent application Ser. No. 11/563,953 filed on Nov. 28, 2006 which claims priority from U.S. Provisional Application No. 60/740,036, filed Nov. 28, 2005, which are both hereby incorporated by reference.

FIELD OF INVENTION

The present invention relates generally to elastic laminates and their methods of manufacture, and, more particularly, to breathable elastic laminates having nonwoven surfaces on both sides.

BACKGROUND OF INVENTION

Breathable elastic laminates are used in the manufacture of many goods, including, for example, disposable articles such as diapers, feminine sanitary articles, and bandages. These applications require that the laminate be strong, stretchable, and soft to the touch. Improving one of these features, however, tends to diminish the others. Consequently, previously-introduced laminates tend to represent a compromise among softness, elasticity, and strength.

For example, one prior art laminate comprises an apertured elastic laminate produced by vacuum laminating a carded polypropylene nonwoven to a multilayer coextruded elastic film. The laminate is then activated in the cross direction using intermeshing gears. This construction has the advantage of a soft feel, but is limited to two layers (nonwoven and film) and lacks high peel strength.

Another prior art product comprises an apertured elastic film which is activated in the cross direction (CD) and is ultrasonically bonded on each side to a consolidated nonwoven. Although this laminate tends to be strong, it has a harsher feel than desired, requires substantial ultrasonic energy to bond the layers, and, because it has three layers, it tends to lack the level of stretch obtainable from a laminate with just a single layer of nonwoven.

Therefore, there is a need for a breathable laminate that is soft on either side yet stretchable and strong. The present invention fulfills this need among others.

SUMMARY OF INVENTION

The invention relates to an elastic laminate having soft, nonwoven surfaces on both sides, yet is stretchable and strong. Specifically, the elastic laminate comprises an elastic inner layer and two outer nonwoven layers, in which each nonwoven layer is rendered extensible through a different method. That is, one nonwoven layer is activated, while the other is consolidated.

Applicants have discovered unexpectedly that the laminate of the present invention has an exceptional degree of cross direction stretch, offers a pleasant, soft feel, and can be bonded ultrasonically at full line speed to obtain an exceptionally strong interlayer bond. Without being bound to any particular theory, applicants hypothesize that the high level of stretch results from "elasticizing" the two nonwoven layers using two different techniques—i.e., activation and consolidation. This approach synergistically combines the strengths of the two technologies, resulting in a laminate having the high tensile strength and a strong bond characteristic of a consolidated/ultrasonically bonded nonwoven, and the softness and tear resistance characteristic of an activated nonwoven. Furthermore, this approach appears to minimize the observed tendency of one nonwoven layer to constrain the extensibility of the other nonwoven layer in the same laminate.

Accordingly, one aspect of the invention is an elastic laminate having two outer nonwoven layers which are rendered extensible using two different techniques. In a preferred embodiment, the elastic laminate comprises: (1) an elastic layer having a first and second side; (2) an activated nonwoven layer bonded to the elastic layer on the first side; and (3) a consolidated nonwoven layer bonded to the elastic layer on the second side.

Another aspect of the invention is a method for producing the laminate described above. In a preferred embodiment, the method comprises: (1) bonding a first nonwoven to an elastic film to form a laminate; (2) activating the laminate to form an activated laminate; and (3) bonding a consolidated nonwoven to the elastic film of the activated laminate to form the elastic laminate.

DETAILED DESCRIPTION OF THE PREFERRED EMBODIMENTS

Figure 1:
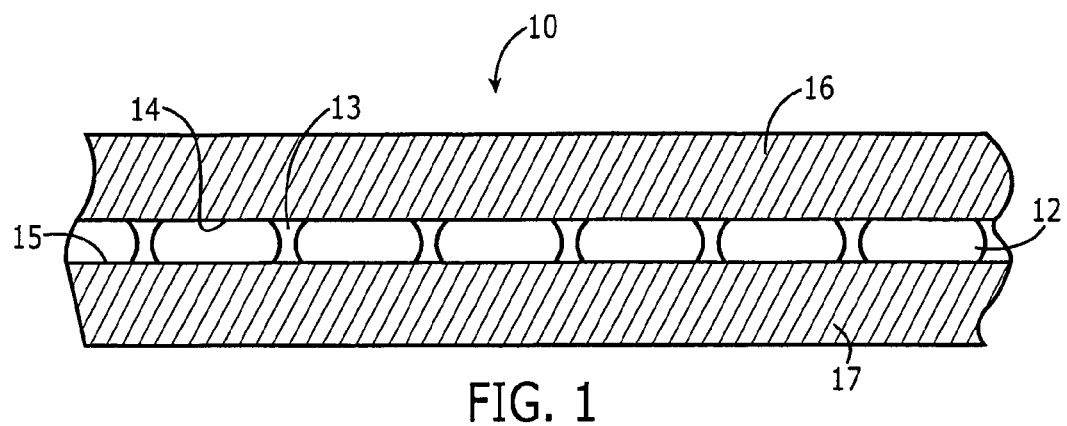
FIG. 1 shows a schematic view of an elastic laminate of the present invention.

The present invention relates to an elastic laminate and a method for making it. Briefly, referring to FIG. 1, the elastic laminate 10 comprises an elastic layer 12 having a first and second side, 14, and 15. Preferably, but not necessarily, the elastic layer has apertures 13 or is otherwise modified to be breathable. On the first side 14 is an activated nonwoven layer 16 bonded to the elastic film material 12. As used herein the terms "activated" or "activation" refer to a method or state in which a laminate comprising an elastic layer and at least one less-elastic layer is stretched to an extension limit beyond the deformation point of the less-elastic layer to allow the elastic layer to elongate to the extension limit essentially unimpeded by the less-elastic layer. Activation is a well-known technique. On the second side 15 is a consolidated nonwoven layer 17 bonded to the elastomer film 12. As used herein, the terms "consolidated" or "consolidation" refer to a method or state in which the fibers or fiber-like elements of the nonwoven are aligned, thereby allowing the nonwoven to elongate in a direction perpendicular to the alignment. Consolidation, like activation, is a well-known technique for imparting extensibility to a nonwoven.

Figure 2:
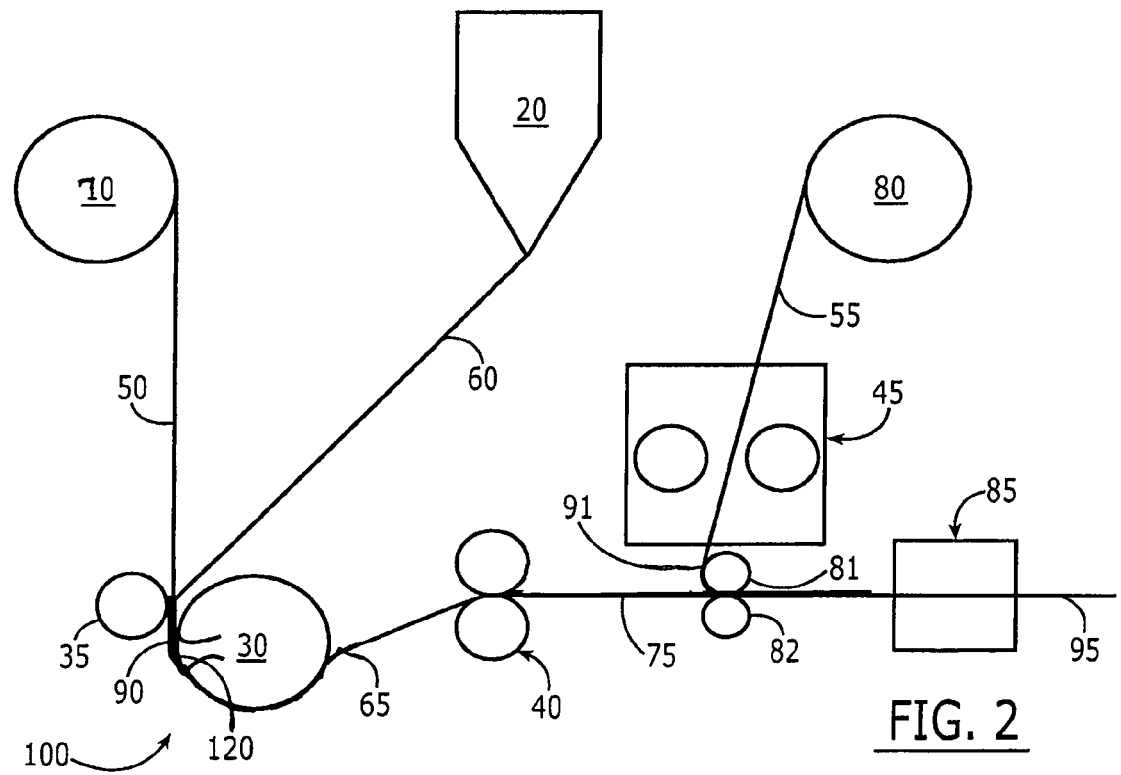
FIG. 2 shows a schematic of a manufacturing line for making the elastic laminate of FIG. 1.

Referring to FIG. 2, the method 100 of preparing the laminate 10 is described in connection with a preferred manufacturing apparatus. The method comprises bonding a first nonwoven 50 to an elastic film 60 to form a laminate 65. The elastic film is optionally breathable. Once the laminate 65 is formed, it is activated to form an activated laminate 75. A consolidated nonwoven 55 is then bonded to the elastic film 50 of the activated laminate 75 to form the elastic laminate 95. The elastic laminate 95, its uses, and the method of preparing it are described in detail below.

Referring back to FIG. 1, the elastic layer 12 provides elasticity to the laminate. The elastic layer comprises at least one elastic material. Suitable elastic materials include any material that is capable of being formed into a thin sheet, rendered breathable and bonded to nonwovens. For example, elastic materials include natural and/or synthetic polymeric materials including isoprenes, butadiene-styrene materials, styrene block copolymers (e.g., styrene/isoprene/styrene (SIS), styrene/butadiene/styrene (SBS), or styrene/ethylene-butadiene/styrene (SEBS)), olefinic elastomers, polyether esters, polyurethanes, etc. In certain preferred embodiments, the elastic materials may comprise high performance elastic material such as Kraton® elastic resins from Kraton Polymers, LLC, which are elastic block copolymers.

The form of an elastic layer 12 can vary and may include, for example, elastic strands, elastic nonwoven, elastic film, elastic adhesive, elastic tacky polymeric web, elastic scrim, etc. For the sake of simplicity, unless otherwise noted, these different forms are referred to collectively herein as "elastic film." In certain preferred embodiments, a monolayer elastic film is used. It should be understood, however, that the present invention in not limited to a monolayer film and, in certain applications, a film having multiple layers may be used. For example, it may be advantageous to have an elastic core between two skin layers to enhance bonding to the nonwoven layers or to facilitate processability. Suitable skin layers are well known and include, for example, polyethylene which may be more or less elastic than the elastic material. The thickness of the elastic film may vary according to the application, although the individual layers of the films are typically thin (e.g., the elastic core is usually, but not necessarily, less than 100 microns, and skin layers, if used, are usually less than 20 microns).

Preferably, the elastic film is breathable or is modified to be breathable in conventional ways. Such ways include, for example, aperturing, slitting, or impregnating with granular particles to create microvoids upon stretching of the elastic film.

The first nonwoven layer 16 provides a soft and breathable surface once activated (discussed below) on the first side 14 of the elastic layer. Suitable nonwovens are capable of being activated and are less elastic than the elastic layer 12. Suitable nonwovens include loose fibers and webs prepared using know techniques such as, for example, air laying, spunbond, spun lace, bonded melt blown, thermobond, bonded carded. The nonwoven material may be homogeneous or contain a variety of woven materials including bi-component fibers (e.g. having an inner core of one material and an outer core of a second material), fibers of different morphologies, geometries, and surface finishes. Suitable nonwovens materials include, for example, fibrous polyolefins such as polyethylenes and polypropylenes, and natural fibers such as cotton and cellulose.

The consolidated nonwoven 17, like the first nonwoven 16, provides a soft and breathable covering to the second side 15 of the elastic layer 12. Unlike the first nonwoven, the consolidated nonwoven is rendered extensible through a consolidation method rather than an activation method. The consolidation method is discussed in detail below.

The laminate 10 may be used in any application requiring a soft, stretchable, breathable material, and especially well suited for disposable articles given its relatively low cost. Suitable applications include, for example, absorbent articles, including adult, child or infant incontinent products (diapers, including parts such as diaper ears, tabs, and/or side panels, briefs, etc.); wraps, including sterile and nonsterile (e.g. bandages with and without absorbent sections,) as well as other disposable and/or multiple use products; e.g., articles proximate to a human or animal body, such as (e.g., garments, apparel, including undergarments, under- and outer-wear, for example, undershirts, bras, briefs, panties, etc., bathing suits, overalls, socks, head coverings and bands, hats, mitten and glove liners, medical clothing, etc.) bed sheets; medical drapes; packaging materials; protective covers; household; office; medical or construction materials; wrapping materials; etc. therapeutic devices and wraps.

The method of making the laminate is described below with reference to FIG. 2. FIG. 2 shows elastic source 20 for providing elastic film 60. In this embodiment, the elastic source 20 comprises a slot die or blown die for extruding molten or semimolten elastic material or coextruding multiple layer film structure in which one or more of the layers are elastic. It should be understood, however, that any conventional elastic source may be used, including, for example, a roll of elastic material.

The first nonwoven source 70 provides the first nonwoven 50. In this embodiment, the first nonwoven source 70 comprises a roll of material, however, any suitable source may be used, including forming the material in situ.

The first nonwoven 50 is brought into contact with elastic film 60 and bonded thereto. In this embodiment, the molten or semimolten phase of elastic film 60 facilitates bonding with the first nonwoven 50. The first nonwoven 50 may also be bound, in whole or part, to the elastic layer using other conventional methods, such as hot pin aperturing, adhesive bonding, thermal bonding, ultrasonic bonding, and combination thereof.

Optionally, the elastic film 60 is modified to render it breathable. One preferred approach for aperturing the elastic layer is shown in FIG. 2 in which a pressure differential source 30 is used. Specifically, the first nonwoven 50 and the elastic film 60 are provided to pressure differential source 30 such that the elastic film 60 is interposed between the pressure differential source 30 and the first nonwoven 50. Pressure differential source 30 creates a pressure differential across the thickness of the laminate which is high enough to cause ruptures (i.e., apertures) in the elastic film 60. This method creates three-dimensional apertures which are especially preferred where breathability or permeability of the laminate is desired.

The pressure differential source 30 is well known. In a preferred embodiment, the pressure differential source 30 comprises a vacuum (not shown) and an aperture definition device 120. In this embodiment, aperture definition device 120 comprises a screen with 20 apertures per linear inch in a square pattern, referred to herein as 20 square. Other screen geometries may be used to vary the amount of open area, aperture size, geometries, patterns, and other attributes. Furthermore, more than one aperture definition device may be used, for example, a device in one area may provide one pattern of apertures, and a device in another area may provide another desired pattern.

In certain embodiments, it may be desired to modify the elastic layer to make it breathable before it is bonded to the first nonwoven layer. Furthermore, it may preferable to use other known aperturing techniques such as pin rolls, slitting, hydrojets, or lasers, instead of or in addition to a pressure differential source to impart permeability or breathability to the laminate. It should also be understood that modifying the elastic film to render it breathable is not required if the elastic film comprises elastic strands or scrim in which case it is already breathable.

Pressure source 35 provides pressure to the materials. A nip roll is used in the preferred embodiments, although any suitable source may be used as a pressure source. Additionally, some embodiments may dispense with a pressure source, or use a pressure differential source as a pressure source as well. Moreover, pressure source 35 is shown here upstream of the pressure differential source, although it may be located adjacent to the pressure differential source 30 or down stream of the pressure differential source 30.

Once the elastic layer is bound to the first nonwoven, it is activated. Referring back to FIG. 2, the laminate 65 is activated in an activation area 40. The activation area 40, in a preferred embodiment, involves intermeshing gear ("IMG") activation, although any conventional activation technique may be used. In the embodiment shown in FIG. 2, activation occurs in the transverse or cross direction (CD), although activation may be in any direction desired, e.g., machine direction (MD), diagonally, or a combination of directions. Further, activation may occur along the entire laminate or only in pre-determined areas of the laminate. In other embodiments, the degree of activation may be varied, for example, a lightly activated area may be used to give a laminate low elasticity, while a heavily activated area may be used to give a laminate high elasticity. Of course, activated regions may be interposed with nonactivated regions as well, to provide zones or regions of extensibility to the laminate.

Returning now to the embodiment of FIG. 1, second nonwoven source 80 provides a second nonwoven 55. In this embodiment, the second nonwoven source 80 comprises a roll of material, although any suitable nonwoven source may be used, such as forming the material in situ.

In one embodiment, the second nonwoven 55 is consolidated on-line. Consolidation may be performed using various techniques such as heat consolation, cold drawing, or combing. Preferably, heat consolidation is used which is disclosed, for example, in U.S. Pat. No. RE 35,206, which is hereby incorporated by reference. As shown in FIG. 2, the second nonwoven 55 passes through heat application area 45, where heat is applied, and the fibers of the web are oriented in the machine direction, thereby providing for elongation in the cross direction. Although consolidation is performed on-line in this embodiment, it should be understood that the consolidation may be performed ahead of time, and a source of consolidated nonwoven be provided to the line.

The consolidated nonwoven 91 is brought into contact with activated laminate 75 through rollers 81 and 82 and bonded using known techniques. Preferably, the consolidated nonwoven 91 and laminate 75 are bonded ultrasonically in the ultrasonic bonding area 85. It has been found that this bonding can be performed quickly at normal line speeds, e.g., 70 mpm.

Varying the materials and method conditions may vary the characteristics of the laminate. For example, selection of particular elastic and/or nonwovens, or selective processing of those materials, can result in optimization of desired properties such as bond strength, softness, elasticity, breathability, etc. Examples of method variables that may be used to modify laminate characteristics include modifying the phase of the elastic layer prior to bonding; modifying the pressure differential applied by a pressure differential source; modifying pressure imposed by a pressure source; modifying apertures in a nonwoven; modifying apertures provided in an aperture definition device; various secondary treatments of the laminate and/or components of the laminate (e.g. plasma treatment), modifying stretching of a laminate following lamination, and combinations thereof. A laminate may also be modified in any suitable fashion, for example, a laminate may be sewn, bonded, printed, cut, shaped, glued, fluted, sterilized, etc.

Laminated to an elastic layer are one or more nonelastic materials. These materials comprise a nonelastic layer in preferred embodiments and are of any suitable material. They are called nonelastic herein to distinguish them from the elastic layer.

Examples of materials used include thermoplastic film material, such as polyethylene, polypropylene, ethylene vinyl acetate and other such polymeric materials; fibrous material (which can comprise a fibrous web, woven and/or non-woven materials, including polyesters, polyolefins, acrylics, rayons, cottons and other cellulose materials, thermoplastic elastomers, and blends of the same, etc.). In preferred embodiments, the nonelastic layers are comprised of a suitable nonwoven layer, such as, for example, polyethylene, polypropylene, etc. The form of a nonelastic layer may be any suitable type, such as, for example, spunbonded, carded, thermobonded, melt blown nonwovens, loose fibers, or a variety of woven materials which comprise different basis weights, fiber compositions, fibers of different geometries, lengths, diameters and surface finishes. Nonelastic materials can also comprise bi-component fibers or various fiber morphologies and geometries (e.g. having an inner core of one material and an outer core of a second material) as well as nonelastics with more than one specific component, for example, a heterogenous nonwoven comprised of more than one component.

Figure 3:
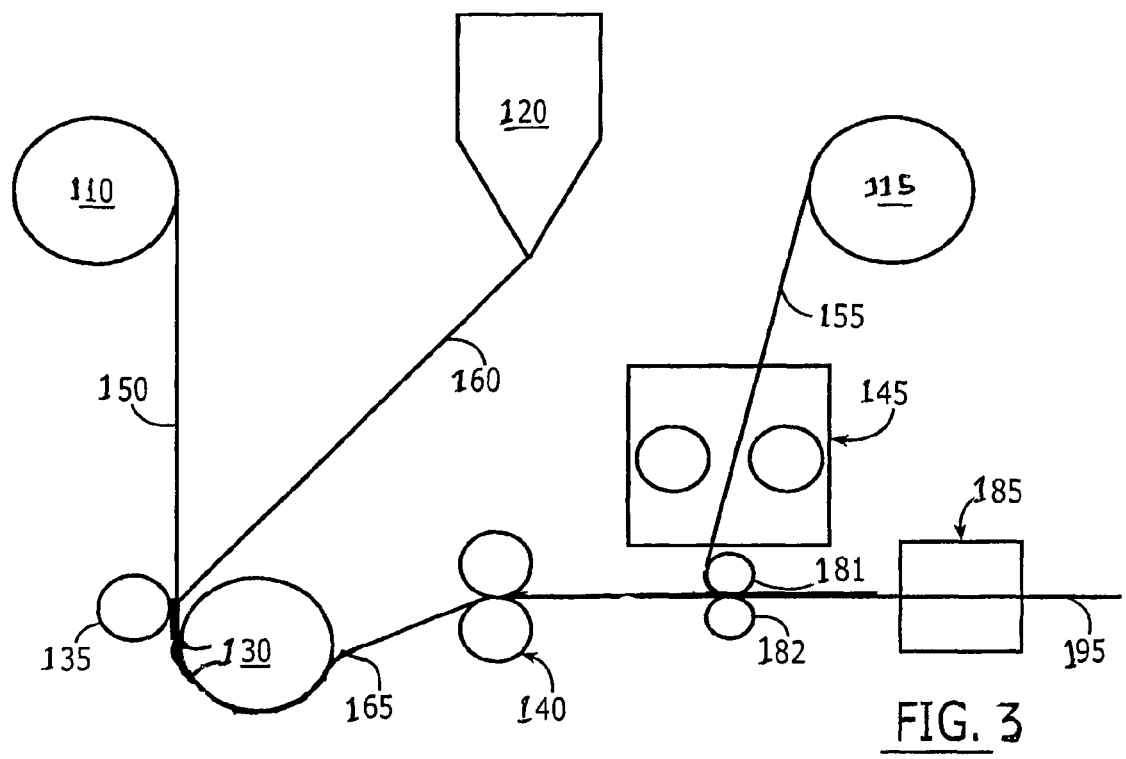
FIG. 3 shows a schematic of a manufacturing line for making an embodiment of the elastic laminate with nonelastic nonwoven layers.

Turning now to FIG. 3, a view of a preferred embodiment is shown. This embodiment provides a breathable elastic trilaminate. First nonelastic source 110 is for providing a first nonelastic material 150. In this embodiment a nonelastic source is shown that comprises a roll of material, however, as was described above any suitable nonelastic material may be used. Therefore, in various embodiments, nonelastic source 10 may be any suitable source according to the material provided. For example, the source may be a pre-formed roll of material, or it may be a piece of equipment (e.g., an extruder) for forming the material in situ.

Returning now to the embodiment of FIG. 3, second nonelastic source 115 is for providing a second nonelastic material 155. In this embodiment a nonelastic source is shown that comprises a roll of material, however, as was described above, any suitable nonelastic material source may be used, such as pre-formed rolls of material, extrusion sources, carding machines, and the like.

It should be noted, that the first nonelastic material and second nonelastic material may be either the same or different materials. Additionally, the materials may vary in physical dimension as well. So for example, a thinner width for a first nonelastic material may be desired, a broader width, etc. Also other characteristics, such as thickness of the laminate, basis weight of the layers, etc. may all be modified as desired.

FIG. 3 also shows elastic source 120, for providing elastic material 160. In this embodiment an elastic source is shown that comprises a slot die or blown die for extruding molten or semimolten elastic material, however, in various embodiments, any suitable source may be used. For example, elastic material used in various embodiments may be a coextruded multiple layer film structure in which one or more of the layers could be elastic. In yet other embodiments, a monolayer elastic film is used. In those embodiments, therefore, an elastic layer is extruded without any additional layers.

FIG. 3 also shows pressure differential source 130. Pressure differential source 30 is for providing a pressure differential to a laminate in order to rupture, at least partially, the laminate, as is further described below. The ruptures in the laminate, in preferred embodiments, are three-dimensional apertures. The apertures are provided in order to allow transfer of air or other fluids as desired, thus providing breathability and fluid permeability to the laminate. The pressure differential source 30 is utilized only when the elastic material 160 is in film form, and is not necessary if elastic strands or scrim are employed as the elastic material 160.

Pressure differential source 130 may be any suitable source. In the preferred embodiments, pressure differential source 130 comprises a vacuum, which results in a greater pressure on one side of the laminate. The vacuum created pressure differential will rupture the laminate and thus provide apertures. An aperture definition device (not shown in FIG. 3) may be used as well. In preferred embodiments, an aperture definition device is employed for providing direction to shape the apertures caused by pressure differential source 130, as will be described further below.

Pressure source 135 for providing pressure to the materials, as will be further described below. A nip roll is used in the preferred embodiments, although any suitable source may be used as a pressure source. Additionally, some embodiments may dispense with a pressure source, or use a pressure differential source as a pressure source as well. Moreover, pressure source 135 is shown here as being present at a certain area; before the area where pressure differential source applies a pressure to the materials. However, it should be noted that a pressure source may also or alternatively be located at other areas, for example, where a pressure differential source applies a pressure differential; below the pressure differential area; etc.

First nonelastic material 110 is brought into contact with elastic material 160. The convention herein is to describe the side on which the first nonelastic is provided as the female side of the elastic. The molten or semimolten phase of elastic material 160 in this embodiment may provide a degree of bonding with first nonelastic material 150. At the point of contact with pressure source 135, the materials may undergo bonding as well, through the pressure imposed by pressure source 135.

The first nonelastic material 110 and the elastic material 160, which are occasionally referred to as laminate 165 hereinafter, then are provided to pressure differential source 130. Elastic material 160 is interposed between the pressure differential source 30 and the first nonelastic material 150. Pressure differential source 130 supplies a differential that is for providing ruptures (i.e., apertures) in the elastic material 160. In certain embodiments, it may be desired to impose a pressure differential on the elastic material 160, only, prior to lamination. Thus, a pressure differential source may rupture the elastic prior to lamination. The rupture is in the form of three-dimensional apertures. These three-dimensional apertures are especially preferred in this embodiment and others where breathability or permeability of the laminate is desired. Embodiments may however, also use other suitable aperturing as desired. For example, embodiments may use a slitting or other process instead of or in addition to a pressure differential source to impart permeability or breathability to the laminate.

Referring back to FIG. 1, laminate 165 passes through activation area 140. Activation area 140 is for providing activation to laminate 165. Activation will allow for stretch of laminated 165, by disrupting any nonelastic layers in various ways depending upon the nature of the material. For example, if a nonelastic layer is a nonwoven, fibers and bonding points between fibers of the nonwoven layers will be disrupted during activation thus freeing any elastic layer to move. Activation, in preferred embodiments, is through intermeshing gear ("IMG") activation. In other embodiments, activation may be provided through any suitable means, such as uniaxial or biaxial orientation, for example.

In the embodiment shown in FIG. 3, activation is occurring in the machine direction (MD), although embodiments may provide activation in any direction desired, e.g., transverse direction (TD) (also known as the cross direction (CD)), diagonally, a combination of directions, etc. Further, activation may occur along the entire laminate, or only in predetermined areas of the laminate.

Returning now to the embodiment of FIG. 3, second nonelastic material 155 comprises a nonwoven web that passes through heat application area 145, where heat is applied and the fibers of the web are consolidated and oriented in the machine direction. This process, which is disclosed in U.S. RE 35,206, provides for a nonwoven web that can be elongated in the cross (or transverse) direction.

The consolidated nonwoven web 155 is brought into contact with laminate 165 through rollers 181 and 182 and ultrasonic area 185 for providing ultrasonic bonding as is known in the art.

Laminate 165 may be used as desired. For example, preferred embodiments provide for side tabs or side panels for diapers, elastic components for adult incontinent products, and other applications.

Activation may occur along the entire laminate, or only in pre-determined areas of the laminate. The characteristics as imparted through activation may be varied as desired. So for example, activation in various preferred embodiments may be in various patterns, locations and/or orientations, in order to provide predetermined characteristics. For example, predetermined stretch characteristics may be provided through particular patterns, locations and/or orientations of stretched laminate. In other embodiments, the degree of activation may be varied, for example, a weakly activated area may be used to give a laminate a weak elasticity, followed by a strongly activated area to give a laminate a strong area of elasticity. Of course, activated regions may be interposed with nonactivated regions as well, so as to provide zones or regions of extensibility to the laminate.

Activation and subsequent modification of predetermined parameters such as stretch characteristics may be within a web intended for manufacturing an article. So for example, regions of varying stretch and/or other characteristics (e.g. breathability) may be provided within a laminate for diaper product construction. Such a laminate might have zones of greater and lesser stretch.

Other methods of lamination may be used as well. For example, nonelastic materials may be bound, in whole or part, using any suitable method, such as hot pin aperturing, adhesive bonding, thermal bonding, ultrasonic bonding, combinations thereof, or any other suitable methods.

As was described above, the nonelastic materials used in various embodiments may be any suitable type and form. Moreover, the nonelastic may be modified as desired as well, e.g., thermally, chemically, mechanically, etc. For example, by providing slits or incisions to the nonwoven material, the mechanical characteristics of extensibility are imparted to the material. Of course, any type of incisions, number of incisions patterns, etc. may be used as desired.

Although the present invention has been described with respect to various specific embodiments, various modifications will be apparent from the present disclosure and are intended to be within the scope of the following claims.

What is claimed is:

1. A method for forming an elastic laminate comprising: extruding an elastic film; applying a first nonwoven to the elastic film; applying a pressure differential to the elastic film and the first nonwoven to bond the first nonwoven web to the elastic film and simultaneously form three-dimensional apertures in the elastic film; activating said bilaminate to deform and elasticize said first nonwoven and to form an activated bilaminate by passing the bilaminate through an activation nip formed of intermeshing gear rollers; and bonding a heat consolidated nonwoven to said elastic film of said activated bilaminate after the bilaminate has passed through the activation nip to form said elastic laminate.

2. The method of claim 1, wherein activating said bilaminate comprises activating said bilaminate in the cross direction.

3. The method of claim 1, wherein said heat consolidated nonwoven is extensible in said cross direction.

4. The method of claim 1, wherein said bonding of said heat consolidated nonwoven is performed ultrasonically.

5. The method of claim 1, wherein said bonding of said heat consolidated nonwoven is performed at essentially the same line speed as said activation step.

6. A method for forming an elastic laminate comprising:
   extruding an elastic film;
   applying a first nonelastic nonwoven layer to the elastic film;
   applying a pressure differential to the elastic film and the first nonelastic nonwoven to bond the nonwoven to the film to form a bilaminate and simultaneously create three-dimensional apertures in the elastic film;
   activating said bilaminate to deform and elasticize said first nonwoven and to form an activated laminate by passing the bilaminate through an activation nip formed of intermeshing gear rollers; and
   bonding a heat consolidated nonelastic nonwoven layer to said elastic film of said activated bilaminate after the bilaminate has passed through the activation nip to form said elastic laminate.

7. The method of claim 6, wherein activating said bilaminate comprises activating said bilaminate in the cross direction.

8. The method of claim 6, wherein said heat consolidated nonelastic nonwoven layer is extensible in said cross direction.

9. The method of claim 6, wherein said bonding of said heat consolidated nonelastic nonwoven layer is performed ultrasonically.

10. The method of claim 6, wherein said bonding of said heat consolidated nonelastic nonwoven layer is performed at essentially the same line speed as said activation step.

* * * * *